(12) United States Patent
Dohi et al.

(10) Patent No.: US 6,428,805 B1
(45) Date of Patent: Aug. 6, 2002

(54) POWDERY NASAL COMPOSITIONS

(75) Inventors: Masahiko Dohi; Yasuhide Uejima; Takao Fujii, all of Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/530,203

(22) PCT Filed: Aug. 24, 1999

(86) PCT No.: PCT/JP99/04560

§ 371 (c)(1),
(2), (4) Date: Apr. 26, 2000

(87) PCT Pub. No.: WO00/12136

PCT Pub. Date: Mar. 9, 2000

(30) Foreign Application Priority Data

Aug. 26, 1998 (JP) .......................................... 10-240242

(51) Int. Cl.[7] ................................................ A61F 13/00
(52) U.S. Cl. ........................ 424/434; 424/489; 424/490; 424/491; 424/494; 424/497; 424/484; 424/486; 424/488

(58) Field of Search ................................ 424/434, 489, 424/491, 494, 497, 484, 486, 488, 490

(56) References Cited

U.S. PATENT DOCUMENTS 5,578,567 A * 11/1996 Cardinaux et al. ............ 514/12

FOREIGN PATENT DOCUMENTS

| JP | 11-130659 | 5/1999 | ............ A61K/9/08 |
| WO | 97/31626 | 9/1997 | ............ A61K/9/14 |
| WO | 98/31343 | 7/1998 | ............ A61K/9/00 |

* cited by examiner

*Primary Examiner*—Thurman K. Page
*Assistant Examiner*—Liliana Di Nola-Baron
(74) *Attorney, Agent, or Firm*—Sughrue Mion, PLLC

(57) ABSTRACT

A powdery nasal composition comprising a drug and colloidal cellulose is provided. The composition is a nasal composition providing a superior absorption activity for the drug.

5 Claims, No Drawings

POWDERY NASAL COMPOSITIONS

This application is a 371 of PCT/JP 99/04560, filed Aug. 24, 1999, the entirety of which is hereby incorporated by reference.

1. Technical Field

The present invention relates to a powdery composition for nasal administration having an improved absorptivity of drugs through the nasal mucosa. More specifically, the present invention relates to a powdery composition for nasal administration that can be easily prepared using a drug and colloidal cellulose, and that can attain a high maximum blood concentration.

2. Background Art

In nonpeptidyl and nonproteinaceous drugs such as anti-inflammatory steroids, for example, there is a need for the development of drugs for nasal administration, because: (1) local nasal mucosa can be the target site of action; (2) an immediate action is desired; (3) some drugs are poorly absorbed through oral administration, and the like.

Many of peptidyl and proteinaceous drugs cannot be readily absorbed in the body because,for example, after oral administration they are decomposed by proteolytic enzymes in the gastrointestinal tract:and the like. In order to use such drugs for treatment of diseases, therefore, they have to be administered via injection in most cases. Injection, however, imposes a considerable burden on patients in terms of pain, the need for hospital visits, and the like. Accordingly, there is a need for the development of noninvasive administration methods such as drugs for nasal administration that can replace injections.

Nasal administration is a method of administration in which drugs are transferred via the nasal mucosa to the blood. Nasal administration is under intensive study as an administration method of the non-injection type, similar to percutaneous administration, ocular administration, rectal administration, pulmonary administration, and the like. Among the non-injection type methods of administration, nasal administration can be easily applied. In addition, since the nasal mucosa has a well-developed blood system as compared to the skin, the ocular mucosa, the rectal mucosa, and the like, nasal administration is considered to have excellent absorptivity of drugs among the non-injection type of methods. Accordingly, nasal administration has been put into practical use for some drugs as pharmaceutical formulations for nasal administration. Furthermore, immediate action equivalent to that of injection can be expected by nasal administration, since it offers the rapid migration of drugs into the blood compared to oral administration. However, the absorptivity of drugs via nasal mucosa depends on the physical properties such as lipophilicity and molecular weight etc. of drugs. Generally, it has been noted that highly water-soluble drugs, highly fat-soluble drugs, and peptidyl and proteinaceous drugs having high molecular weights have low absorptivity. Accordingly, various ideas have been proposed to enhance the absorptivity;of these drugs via nasal mucosa.

For example, Suzuki et al. (Japanese Examined Patent Publication (Kokoku) No. 60-34925) report a sustained-release formulation for the nasal cavity comprising a cellulose ester and a drug.

The sustained-release formulation for the nasal cavity of the above Patent Publication is intended to adhere to the nasal mucosa so as to gradually release the drug for an extended period of time, thereby enabling the absorption of the drug via the nasal mucosa and a sustained-release of the effective amount thereof. However, since the sustained-release formulation for the nasal cavity of the above Patent Publication focuses on the slow release of the drug, the formulation is considered not to have a sufficient function of promoting the absorption of the drug. Besides, the preferred embodiments of the drug are anti-inflammatory steroids, analgesic anti-inflammatory drugs, anti-histamine drugs, and drugs having anti-allergy actions, i.e., drugs for which the maintenance of the local concentration of the drug is important rather than the absorptivity into the systemic blood circulation.

Thus, the sustained-release formulations for the nasal cavity of the above Patent Publication are not expected to have high absorptivity via the nasal cavity for highly water-soluble drugs, highly fat-soluble drugs, and peptidyl and proteinaceous drugs having high molecular weights. Thus, there is a need for the development of compositions for administration to the nasal mucosa in which these drugs can be effectively used in terms of therapeutic effects and therapeutic efficiency.

Nolte et al. (Hormone Metabolic Research Vol. 22, 170–174, 1991) and Bruice et al. (Diabetic Medicine Vol. 8, 366–370, 1991) report on insulin formulations for nasal administration that contain an absorption-promoting agent such as sodium glycolate or sodium taurofusidate. However, due to a problem of irritation of the nasal mucosa, these absorption-promoting agents have not been put into practical use.

It has already been disclosed in the specifications of Japanese Examined Patent Publication (Kokoku) No. 62-42888 and WO97/31626 that a combination of crystalline cellulose which is a component of colloidal cellulose, and a viscosity-increasing agent is effective for nasal administration.

Suzuki et al. (Japanese Examined Patent Publication (Kokoku) No. 62-42888) report on a powdery composition for nasal administration having an excellent absorptivity via the nasal mucosa, said composition comprising a polypeptide and a water-absorbing and low water-soluble base. They also report that such a composition permits the nasal absorption of polypeptides without using an absorption-promoting agent.

However, even for the compositions of the above Patent Publication, the nasal absorption ratio (area under the curve (AUC) of blood concentration along the time after nasal administration) of polypeptides never exceeds 10–20% that after injection administration. According to Example 4 of the above Patent Publication, for example, the maximum blood concentration after the administration of 10 units of insulin to rabbits is 200, $\mu$U/ml or lower, or about 20% that of the injection administration of the same unit, and the absorption ratio determined from AUC thereof is estimated to be 10% or lower.

The Patent Publication further describes the combined use of a water-absorbing and water-soluble base, and a water-absorbing and low water-soluble base at a ratio of 0.1-60% by weight, most preferably 1-50% by weight based on the weight of the water-absorbing and low water-soluble base. However, as the object and effects. of the combined use, it only states the effect of slow release (slow and sustained) compared to the use of the water-absorbing and low water-soluble base alone. Furthermore, the Patent Publication makes no mention of using nonpeptidyl and non-proteinaceous drugs instead of polypeptides.

The specification of WO97/31626 describes that, by combining a plurality of water-absorbing and low water-soluble bases including crystalline cellulose and a plurality of water-absorbing and water-soluble bases, including hydroxypropyl cellulose, powdery compositions for nasal administration that exhibit an excellent maximum blood concentration can be provided for various drugs, i.e. peptidyl and proteinaceous drugs and nonpeptidyl and nonproteinaceous drugs.

However, in the above cases the combination of components is same as colloidal cellulose and the building components are identical, but the above components merely mixed as disclosed in the above two Patent Publications are different from a colloidal cellulose that is an essential component of the present invention, and therefore these Patent Publications make no mention of the present invention. For example, though one of the features of colloidal cellulose is that it can be well dispersed in an aqueous medium so as to form a stable suspension, it is well known to a person skilled in the art that the effect is different from and much superior to a simple mixture of crystalline cellulose and a viscosity-increasing agent as described in a pamphlet for Avicel manufactured by Asahi Chemical Industry Co., Ltd. Accordingly, the disclosure in the above Patent Publications cannot be considered to make any suggestion regarding the present invention.

Peptidyl and proteinaceous drugs are generally expensive. Furthermore, the expected therapeutic effects cannot be obtained in many cases due to their low absorptivity and large variations in blood concentrations. There is a need, therefore, for compositions for nasal administration comprising peptidyl and proteinaceous drugs having better absorptivity. There is also a need for compositions for nasal administration that are safe and that have better absorptivity. There is also a need for compositions for nasal administration that can provide higher blood concentrations. The same holds true for nonpeptidyl and nonproteinaceous drugs.

DISCLOSURE OF THE INVENTION

As described above, although the nasal administration of drugs has various merits as a method of administration, there is much room for improvement in terms of absorptivity, maximum blood concentration, and the like. Thus, it is an object of the present invention to provide compositions for nasal administration that have excellent absorptivity of drugs.

It is also an object of the present invention to provide compositions for nasal administration that exhibit excellent absorptivity, in particular much higher maximum blood concentrations.

It is a further object of the present invention to provide compositions for nasal administration that exhibit excellent absorptivity, in particular much higher maximum blood concentrations, of highly water-soluble drugs, highly fat-soluble drugs, and peptidyl and proteinaceous drugs having high molecular weights.

It is a still further object of the present invention to provide compositions for nasal administration that exhibit excellent absorptivity, in particular much higher maximum blood concentrations, of drugs that originally have good nasal absorptivity such as highly water-soluble drugs, highly fat-soluble drugs, and nonpeptidyl and nonproteinaceous drugs having high molecular weights.

Furthermore, it is an object of the present invention to provide safe compositions for nasal administrations in these compositions for nasal administrations.

In intensive efforts to solve the above problems, the present inventors have found that by using a drug and colloidal cellulose, it is possible to provide a novel powdery composition for nasal administration having excellent absorptivity for those drugs and nonpeptidyl and nonproteinaceous drugs that had low nasal absorptivity, in particular a novel powdery composition for nasal administration with which a significantly high maximum blood concentration can be obtained, and thereby have accomplished the present invention.

Thus, the present invention provides a powdery composition for nasal administration comprising a drug and colloidal cellulose.

Embodiment for Carrying Out the Invention

Preferred examples of the drugs of the present invention preferably include nonpeptidyl and nonproteinaceous drugs and peptidyl and proteinaceous drugs.

As nonpeptidyl and nonproteinaceous drugs, a wide range of nonpeptidyl and nonproteinaceous drugs are available. Specific examples include anti-inflammatory steroids or non-steroidal anti-inflammatory drugs, analgesic anti-inflammatory drugs, sedatives, anti-depressants, antitussive expectant drugs, anti-histamine drugs, anti-allergic drugs, antiemetic drugs, hypnotic drugs, vitamins, sex steroid hormones, anti-cancer drugs, anti-arrhythmic drugs, anti-hypertensive drugs, anti-anxiety drugs, psychomimetics, anti-ulcer drugs, cardiac stimulants, analgesics, bronchodilatiors, anti-obesity drugs, platelet aggregation suppressive drugs, antidiabetic drugs, muscle relaxants, anti-migraine drugs, antirheumatic drugs, and the like. As nonpeptidyl and nonproteinaceous drugs, one or more of those selected from the group consisting of the above can be used. Among them, preferred examples include antiemetic drugs, hypnotic drugs, vitamins, sex steroid hormones, anti-migraine drugs, analgesics, and the like.

More specifically, examples of such nonpeptidyl and proteinaceous drugs include: anti-inflammatory steroids or non-steroidal anti-inflammatory drugs such as hydrocortisone, prednisolone, triamcilnolone, dexamethasone, betamethasone, beclomeithasone, fluticasone, mometasone, fluocortin, budesonide, salbutamol, and salmeterol; analgesic anti-inflammatory drugs such as acetaminophen, phenacetin, aspirin, aminopyrine, sulpyrine, phenylbutasone, mefenamic acid, flufenamic acid, ibufenac, ibuprofen, alclofenac, diclofenac, and indometacin; sedatives such as scopolamine; antidepressants such as imipramine; antitussive expectrant drugs such as sodium cromoglycate, codeine phosphate, and isoproterenol,hydrochloride; anti-histamine drugs such as diphenhydramline, triprolidine, isothipendyl, and chlorpheniramine; anti-allergic drugs such as amlexanox, azelastine, ozagrel, tranilast, and ketotifen; anti-emetic drugs such as; ondansetron, granisetron, metoclopramide, cisapride, and domperidone; hypnotic drugs such as brotizolam and melatonine; vitamins such as cyanocobalamine and mecobalamine; sexual steroid hormones such as estradiol, estritol, progesterone, and testosterone; anti-cancer drugs such as tamoxiphene and tegafur; anti-arrhythmic drugs such as propranolol and atenolol; anti-hypertensive drugs such as nicardipine; anti-anxiety drugs such as diazepam; psychomimetics such as nitrazepam; anti-ulcer drugs such as cimetidine and ranitidine; cardiac stimulants such as dopamine; analgesics such as morphine and buprenorphine; bronchodilators such as oxitropium and ozagrel; anti-obesity drugs such as mazindol; platelet aggregation suppressive drugs such as beraprost, and carbacyclin;, antidiabetic drugs such as acarbose and sorbitol; muscle relaxants such as pinaverium and inaperisone; anti-migraine drugs such as ergotamine, imigran, and alniditan; antirheumatic drugs such as actarit and platonin.

The peptidyl and proteinaceous drugs of the present invention are preferably those of which molecular weight does not exceed 30,000. As peptidyl and proteinaceous drugs of which molecular weight does not exceed 30,000, there may be mentioned, for example, luteinizing hormone-releasing hormones, growth hormone-releasing factors, somatostatin derivatives, vasopressins, oxytocins, hirudin derivatives, enkephalins, adrenocorticotrophic hormone derivatives, bradykinin derivatives, calcitonins, insulins, glucagon derivatives, growth hormones, growth hormone-releasing hormones, luteinizing hormones, insulin-like growth hormones, calcitonin gene-related peptides, atrial natriuretic peptide derivatives, interferons, interleukins, erythropoietins, granulocyte colony-stimmulating factor, macrophage forming stimulating factor, parathyroid hormones, parathyroid hormone-releasing hormone, prolactin, thyroid stimulating hormone-releasing hormone, and angiotensins. As the peptidyl and proteinaceous drugs of the present invention, one or more of those selected from the group consisting of these specific examples can be used.

According to the present invention, the particle diameter of the drugs is preferably less than 150 $\mu$m. More preferably the diameter is less than 50 $\mu$m wherein the effects are further enhanced. However, drugs which are too finely pulverized, though showing enhanced absorption promoting effects, pose a problem of pharmaceutical handling due to scattering, etc., and a more preferred diameter of the drugs is 0.5 $\mu$m or greater and less than 10 $\mu$m.

As a method of rendering the diameter of particles of the drugs 10 $\mu$m, there can be mentioned the pressurized type of pulverization by mortars etc., the rotating impact type of pulverization by centrifugation etc., recrystalization by a spray drier, a lyophilizer etc.

The colloidal cellulose of the present invention is a colloidal cellulose obtained by, for example, spray-drying one or more of viscosity-increasing agents and crystalline cellulose, said viscosity-increasing agents comprising carboxymethylcellulose, sodium salts of carboxymethylcellulose, calcium salts of carboxymethylcellulose, xanthan gum, hydroxypropyl cellulose, hydroxypropyl methyl cellulose, acrylic acid starch, and the like. Among them, colloidal celluloses comprising crystalline cellulose and a sodium salt of carboxymethylcellulose or xanthan gum are commercially available from Asahi Chemical Industry Co., Ltd. as Avicel RC-581, Avicel RC-591, and Avicel CL-611, Avicel RC-N81, etc., which are preferred since they have already been put into practical use in pharmaceutical formulations.

Avicel RC-581 and Avicel RC-591 are each composed of crystalline cellulose and CMCNa at a mixed weight ratio of 89/11, and AvicelCL-611- at a ratio of 85/15, which are trade marks of products of Asahi Chemical Industry Co., Ltd. Similarly, AvicelRC-N81 is a!special mixture of crystalline cellulose and a natural polysaccharide and is a trade mark of products of Asahi Chemical Industry Co., Ltd. These are colloidal cellulose made by the production method as described above, and have distinct properties different from those of physical mixtures of cellulose and CMCNa. For example, according to technical documents of Asahi Chemical Industry Co., Ltd., colloidal cellulose has features that: (1) it has excellent suspension stability, (2) it has excellent emulsion stability, (3) the dispersion solution thereof exhibits thixotropy, and the like. It is clear to a person skilled in the art that these features are evidently different from those of crystalline cellulose itself or physical mixtures of cellulose and CMCNa.

The composition of the present, invention may be prepared by, for example, a method of mechanically mixing colloidal cellulose and a drug.

Mechanical mixing as used herein refers to mixing with a mixer of the fixed vessel type such as a high speed mixer or a mixer of the rotary type such as a V-type mixer. Specifically, mixing with the fixed vessel type is preferred since. it significantly enhances the effects of the present invention.

As used herein, mixers of the fixed vessel type include universal mixers, ribbon mixers, automatic mortars, ball mills, and other mixers such as high speed mixers, power fully automatic mixers, etc., as well as manual pressurized mixing with mortars. Mixers of the rotary vessel type are V-shaped mixers, cross rotary mixers, double-coned mixers, and the like.

The amount of the drug for use in the present invention is a therapeutically effective amount, and may be decided depending on the drug administered, the kind and degree of the disease to be treated, the age and weight of the patient, and the like. Generally, the amount is equal to 20 times that used for injection administration, and more preferably equal to 10 times.

Since the amount of the powder that can be applied to the nasal cavity is limited and depends on the amount required for treatment, the amount of colloidal cellulose cannot be generally specified, but it is preferably an equal amount to one weight part of the drug, most preferably 5 or more weight parts and more preferably 10 or more weight parts per weight part of the drug.

In order to improve the physical property, appearance, or smell etc. as a pharmaceutical formulation of the composition of the present invention, known lubricants, binders, diluents, colorants, preservatives, antiseptics, corrigents, and the like can be added as desired. As lubricants, there can be mentioned, for example, talc, stearic acid and salts thereof, wax, and the like; as binders, starch, dextrin, and the like; as diluents, starch, lactase, and the like; as colorants, Red No. 2 and the like; as preservatives, ascorbic acid and the like; as antiseptics, paraoxybenzoic acid esters and the like; as corrigents, menthol and the like.

The composition of the present invention may be formulated into a suitable dosage form in order to be administered as a pharmaceutical formulation. An example of such a dosage form is a capsule in which the present invention has been filled by each dosage unit, which is sprayed into the nasal cavity using a suitable dispenser. The composition of the present invention at an amount for unit dosage or at an amount for multiple doses is dispensed in a suitable container, and the composition of the present invention may be administered at an amount for unit dosage given at one time or in divided doses.

Thus, in accordance with the present invention, a powdery composition for nasal administration having excellent absorptivity via the nasal cavity and a significantly higher maximum blood concentration than the conventional compositions for nasal administrations can be provided for highly water-soluble drugs, highly fat-soluble drugs, and peptidyl and proteinaceous drugs having high molecular weight.

According to the powdery composition for nasal administration of the present invention, it is possible to obtain significantly-higher maximum blood concentration at an amount equal to the conventional amount for nonpeptidyl and nonproteinaceous drugs as well as expensive peptidyl and proteinaceous drugs. Accordingly, the amount used of the drug can be reduced. Furthermore, it is possible to stably obtain the desired therapeutic effect by minimizing variation in blood concentrations.

Furthermore, the powdery composition for nasal administration of the present invention has an excellent absorptivity (sustained blood concentration) similarly to the conventional powdery compositions for nasal administrations, and it obviates the need of using specifically absorption-promoting agents that have an irritating nature and therefore it is safe, and it is expected that the desired therapeutic effect can be stably obtained.

Therefore, it is believed that the present invention is highly valuable for drug therapy by the administration of non-injection type drugs.

EXAMPLES

The present invention will now be, explained in more detail with reference to specific examples. It is to be noted that the present invention is not limited by these examples in any way.

Examples 1 to 8

According to Table 1, the composition of the present invention was prepared by mixing each drug and colloidal cellulose (Avicel RC-591) in a mortar.

TABLE 1

| | Drug | Amount of drug | Collodial cellulose | Amount of colloidal cellulose |
|---|---|---|---|---|
| Example 1 | Buprenorphine hydrochloride | 40 | Avicel RC-591 | 2000 |
| Example 2 | Ergotamine tartarate | 100 | Avicel RC-591 | 2000 |
| Example 3 | Beclomethasone propionate | 5 | Avicel RC-591 | 2000 |
| Example 4 | Estradiol | 20 | Avicel RC-591 | 2000 |
| Example 15 | Leuprolide acetate | 10 | Avicel RC-591 | 2000 |

TABLE 1-continued

| | Drug | Amount of drug | Collodial cellulose | Amount of colloidal cellulose |
|---|---|---|---|---|
| Example 6 | Salmon calcitonin | 2 | Avicel RC-591 | 2000 |
| Example 7 | Carboxy fluorescein | 10 | Avicel RC-591 | 1000 |
| Example 8 | FITC-dextran (MW = 400) | 20 | Avicel RC-591 | 1000 |

Comparative Examples 1 to 8

Powdery compositions (each designated as Comparative Examples 1-1 to 8-1 corresponding to Examples 1 to 8) were prepared from each drug used in Examples 1 to 8 and crystalline cellulose instead of colloidal cellulose, and solutions or dispersions (each designated as Comparative Examples 1-2 to 8-2 corresponding to Examples 1 to 8) were prepared by dissolving or dispersing each drug used in Examples 1 to 8 in water. Furthermore, powdery compositions (each designated as Comparative Examples 1-3, 5-3, and 6-3 corresponding to Examples 1, 5, and 6) were prepared from each drug used in Example 1,5, and 6 and a physical mixture comprising crystalline cellulose instead of colloidal cellulose and sodium carboxymethylcellulose (CMCNa).

The above preparations were given to the nasal cavity of conventional white male; rabbits (body weight 2.5–3.0 kg) using a nebulizer (Publizer-manufactured by Teijin Ltd.) to an amount of the composition at 8 mg/kg. After a certain period of time, blood was drawn from the ear vein, and the blood concentration was determined using the HPLC method or the RIA method.

The result is shown in Table 2.

TABLE 2

| | | | Time course of blood concentration of the drug after administration | | | | |
|---|---|---|---|---|---|---|---|
| Drug | Base | Formulation | 15 min | 30 min | 60 min | 90 min | Units |
| Ex. 1 | BN | MCC + CMCNa | Powder | 6.4 | 5.0 | 3.2 | 1.8 | ng/ml |
| Com. Ex. 1-1 | BN | MCC | Powder | 2.9 | 3.2 | 1.7 | 0.5 | ng/ml |
| Com. Ex. 1-2 | BN | — | Liquid | 0.5 | 1.0 | 0.4 | 0.2 | ng/ml |
| Com. Ex. 1-3 | BN | MCC, CMCNa | Powder | 4.3 | 3.2 | 1.8 | 0.8 | ng/ml |
| Ex. 2 | ER | MCC + CMCNa | Powder | 90 | 77 | 54 | 23 | ng/ml |
| Com. Ex. 2-1 | ER | MCC | Powder | 53 | 40 | 20 | 10 | ng/ml |
| Com. Ex. 2-2 | ER | — | Liquid | 15 | 20 | 12 | 8 | ng/ml |
| Ex. 3 | BDP | MCC + CMCNa | Powder | 100 | 80 | 65 | 40 | pg/ml |
| Com. Ex. 3-1 | BDP | MCC | Powder | 85 | 62 | 40 | 30 | pg/ml |
| Com. Ex. 3-2 | BDP | — | Liquid | 10 | 12 | 5 | 2 | pg/ml |
| Ex. 4 | E2 | MCC + CMCNa | Powder | 420 | 270 | 180 | 60 | pg/ml |
| Com. Ex. 4-1 | E2 | MCC | Powder | 290 | 300 | 180 | 40 | pg/ml |
| Com. Ex. 4-2 | E2 | — | Liquid | 100 | 60 | 10 | 5 | pg/ml |

TABLE 2-continued

Time course of blood concentration of the drug after administration

| | Drug | Base | Formulation | 15 min | 30 min | 60 min | 90 min | Units |
|---|---|---|---|---|---|---|---|---|
| Ex. 5 | LP | MCC + CMCNa | Powder | 180 | 145 | 96 | 50 | ng/ml |
| Com. Ex. 5-1 | LP | MCC | Powder | 120 | 110 | 80 | 28 | ng/ml |
| Com. Ex. 5-2 | LP | — | Liquid | 10 | 5 | 0 | 0 | ng/ml |
| Com. Ex. 5-3 | LP | MCC, CMCNa | Powder | 140 | 120 | 80 | 30 | ng/ml |
| Ex. 6 | sCT | MCC + CMCNa | Powder | 320 | 190 | 80 | 40 | pg/ml |
| Com. Ex. 6-1 | sCT | MCC | Powder | 120 | 200 | 75 | 30 | pg/ml |
| Com. Ex. 6-2 | sCT | — | Liquid | 25 | 10 | 0 | 0 | pg/ml |
| Com. Ex. 6-3 | sCT | MCC, CMCNa | Powder | 200 | 180 | 80 | 40 | pg/ml |
| Ex. 7 | CF | MCC + CMCNa | Powder | 10 | 15 | 8 | 5 | ng/ml |
| Com. Ex. 7-1 | CF | MCC | Powder | 5 | 6 | 3 | 3 | ng/ml |
| Com. Ex. 7-2 | CF | — | Liquid | 1 | 0 | 0 | 0 | ng/ml |
| Ex. 8 | DX | MCC + CMCNa | Powder | 12 | 8 | 8 | 4 | ng/ml |
| Com. Ex. 8-1 | DX | MCC | Powder | 6 | 8 | 5 | 4 | ng/ml |
| Com. Ex. 8-2 | DX | — | Liquid | 0 | 0 | 0 | 0 | ng/ml |

Note:
BN means buprenorphine hydrochloride, ER means ergotamine tartarate, BDP means beclomethasone propionate, E2 means estradiol, LP means leuprolide acetate, sCT means salmon calcitonin, CF means carboxyfluorescein, DX means FITC-dextran (MW = 4,400), MCC + CMCNa means Avicel RC-591, MCC means crystalline cellulose (Avicel (Tm) PH-101), CMCNa means sodium carboxymethylcellulose, respectively.

As can be seen from the above Table 2, the blood concentration of the drug for powders comprising a mixture of the drug and MCC and liquids that are aqueous solutions or aqueous dispersions of the same drug was significantly low as compared to that provided by the administration into the nasal cavity of the pharmaceutical composition of the present invention prepared from the drug and colloidal cellulose (MCC +CMCNa; Avicel RC-591). The blood concentration of the drug for powders prepared using a physical mixture of MCC instead of colloidal cellulose and CMCNa was lower than that of the pharmaceutical composition of the present invention.

This means that colloidal cellulose has a synergistic effect that cannot be expected from physical mixtures of MCC and CMCNa for the nasal absorption of drugs.

What is claimed is:

1. A powdery nasal composition comprising a drug and colloidal cellulose, wherein said colloidal cellulose is obtained by spray-drying crystalline cellulose and one or more viscosity-increasing polymers selected from the group consisting of carboxymethylcellulose, a sodium salt of carboxymethylcellulose, a calcium salt of carboxymethylcellulose, xantha gum, hydroxypropyl cellulose, hydroxypropyl methyl cellulose, and acrylic acid starch.

2. The powdery nasal composition according to claim 1 wherein said drug is a nonpeptidyl and nonproteinaceous drug or a peptidyl and proteinaceous drug.

3. The powdery nasal composition according to claim 2, wherein said nonpeptidyl and nonproteinaceous drug is one or more of the drugs selected from the group consisting of anti-inflammatory steroids or non-steroidal anti-inflammatory drugs, analgesic anti-inflammatory drugs, antitussive expectorant drugs, anti-histamine drugs, anti-allergic drugs, anti-emetic drugs, hypnotic drugs, vitamins, sex steroid hormones, anti-cancer drugs, anti-arrhythmic drugs, anti-hypertensive drugs, anti-anxiety drugs, psychomimetics, anti-ulcer drugs, cardiac stimulants, analgesics, bronchodilators, anti-obesity drugs, platelet aggregation suppressive drugs, anti-diabetic drugs, muscle relaxants, anti-migraine drugs, and anti-rheumatic drugs.

4. The powdery nasal composition according to claim 2, wherein said peptidyl and proteinaceous drug is one or more of the drugs selected from the group consisting of luteinizing hormone-releasing hormones, growth hormone-releasing factors, somatostatin derivatives, vasopressins, oxytocins, hirudin derivatives, enkephalins, adrenocorticotrophic hormone derivatives, bradykinin derivatives, calcitonins, insulins, glucagon derivatives, growth hormones, growth hormone-releasing hormones, luteinizing hormones, insulin growth hormones, calcitonin gene-related peptides, atrial natriuretic peptide derivatives, interferons, erythropoietins, granulocyte colony-stimulating factor, macrophage forming stimulating factor, parathyroid hormones, parathyroid hormone-releasing hormone, prolactin, thyroid stimulating hormone-releasing hormone, and angiotensins.

5. A powdery nasal composition comprising a drug and colloidal cellulose obtained by spray-drying crystalline cellulose and one or more viscosity-increasing polymers selected from the group consisting of carboxymethylcellulose, a sodium salt of carboxymethylcellulose, a calcium salt of carboxymethylcellulose, xanthan gum, hydroxypropyl Cellulose, hydroxypropyl nethyl cellulose, and acrylic acid starch, wherein said colloidal cellulose is one or more colloidal celluloses selected front the group consisting of Avicel RC-581, Avicel RC-591, and Avicel CL-611.

* * * * *